United States Patent [19]

Björk et al.

[11] 4,447,433
[45] * May 8, 1984

[54] DIPHENYLBUTYL-PIPERAZINECARBOXA-MIDES TO TREAT PAIN

[75] Inventors: Anders K. K. Björk, Bjärred; Knut G. Olsson, Malmö; Aina L. Abramo, Bjärred; Erik G. Christensson, Lund, all of Sweden

[73] Assignee: AB Ferrosan, Malmo, Sweden

[*] Notice: The portion of the term of this patent subsequent to May 24, 2000 has been disclaimed.

[21] Appl. No.: 418,685

[22] Filed: Sep. 15, 1982

Related U.S. Application Data

[60] Division of Ser. No. 227,690, Jan. 23, 1981, Pat. No. 4,385,057, which is a continuation-in-part of Ser. No. 86,068, Oct. 18, 1979, Pat. No. 4,308,387.

[30] Foreign Application Priority Data

Oct. 20, 1978 [SE] Sweden .............................. 7810971

[51] Int. Cl.³ .......................................... A61K 31/495
[52] U.S. Cl. .................................................. 424/250
[58] Field of Search ......................................... 424/250

Primary Examiner—Stanley J. Friedman
Attorney, Agent, or Firm—Abelman, Frayne, Rezac & Schwab

[57] ABSTRACT

Compounds having the general formula

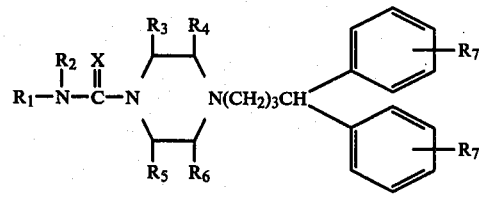

as herein defined and pharmaceutically acceptable acid addition salts thereof. Pharmaceutical compositions containing said compounds. Methods of treatment of humans and animals by such compounds and compositions.

3 Claims, 4 Drawing Figures

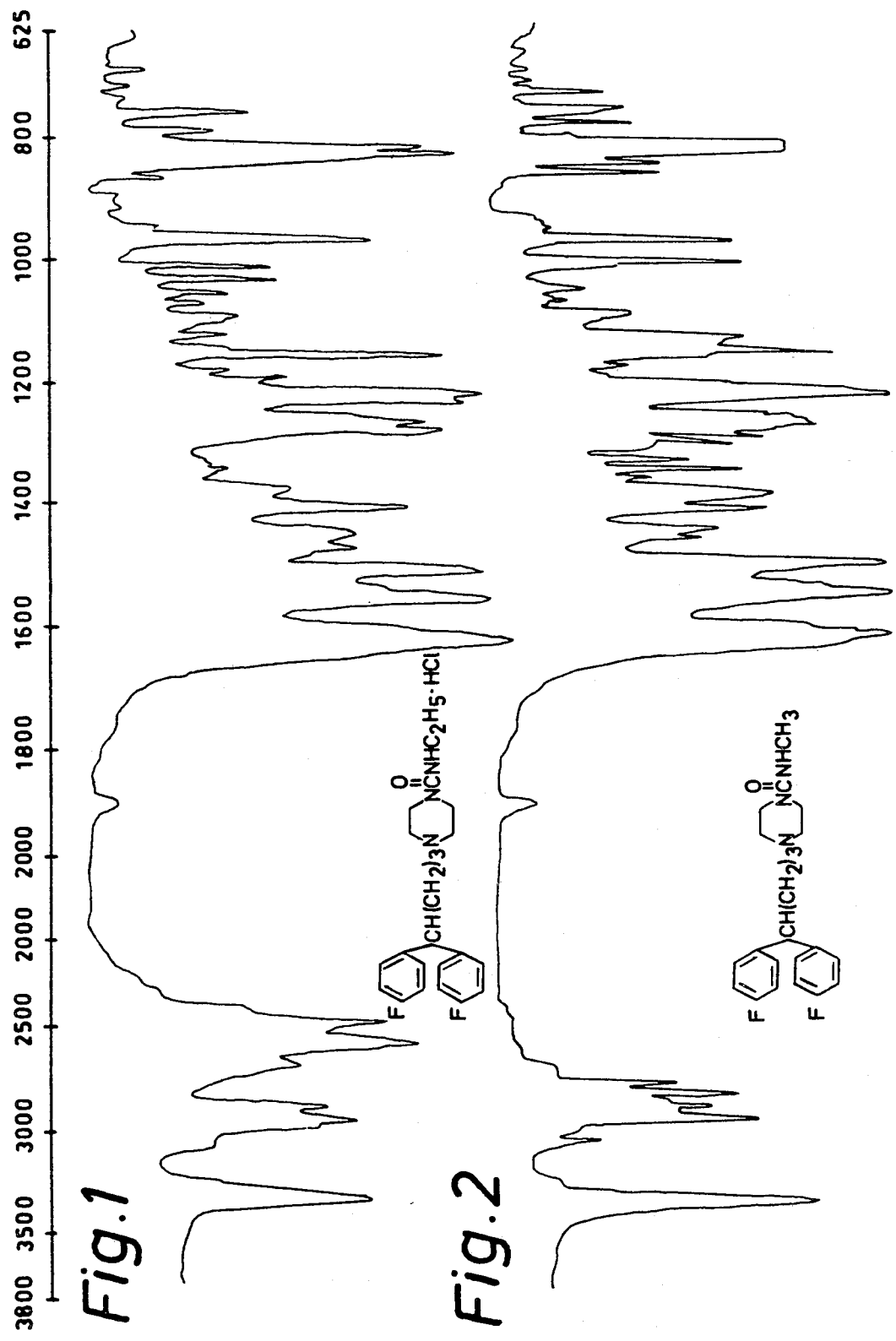

DIPHENYLBUTYL-PIPERAZINECARBOXAMIDES TO TREAT PAIN

This application is a Rule 60 divisional Application of Ser. No. 227,690, filed Jan. 23, 1981, now U.S. Pat. No. 4,385,057, which is a continuation-in-part Application of Ser. No. 086,068, filed Oct. 18, 1979, now U.S. Pat. No. 4,308,387.

This invention relates to a novel class of N',N',2,3,4,5,6-substituted 1-piperazine-carboxamides and carbothioamides, acid addition salts thereof, pharmaceutical compositions containing the same, and methods of making and using the same.

Most drugs used today in the treatment of different mental disorders are contained in the groups of major tranquillisers, i.e. neuroleptics, antidepressants and anxiolytics. All said drugs have been shown to be useful in the treatment of mental disorders, but they also induce several side effects, e.g. the severe extrapyramidal side effects induced by the neuroleptics, the cardiovascular side effects caused by the antidepressants and the dependence and abuse induced by the anxiolytics. The new compounds of formula I have a pharmacological profile not seen in any compound described earlier. They are characterized by a strong influence on limbic, hypothalamic and pituital areas of the brain. These brain areas are known to be involved in regulation of emotional behaviour, aggression, mood, fear and anxiety. Furthermore, these brain areas besides in many autonomic and somatic functions also participate in the regulation of sexual behaviour, cognitive behaviour, motivation, exploratory behaviour, learning and memory processes. Therefore they are important for disorders such as schizophrenia, depressions, anxiety, psychosomatic disorders as well as geriatric disorders.

The novel 1-piperazine-carboxamides and carbothioamides according to the invention may be structurally represented by the general formula I

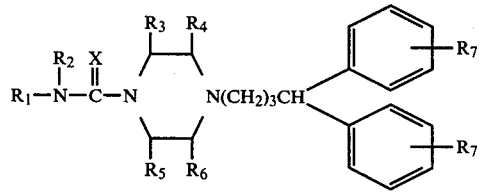

wherein $R_1$ and $R_2$ are groups independently selected from the group of hydrogen, alkyl straight or branched chains having from 1 to 10 carbon atoms, cycloalkyl having from 3 to 8 carbon atoms, aralkyl having from 7 to 9 carbon atoms, alkenyl having from 2 to 10 carbon atoms, phenyl unsubstituted or substituted by one to three substituents selected from halogen, including F, Cl and Br, lower alkyl having from 1 to 5 carbon atoms, lower alkoxy having from 1 to 5 carbon atoms, amine unsubstituted or substituted by one or two lower alkyl groups having from 1 to 5 carbon atoms, —$CF_3$ and —CN groups, $R_3$, $R_4$, $R_5$ and $R_6$ are groups independently selected from hydrogen, lower alkyl having from 1 to 3 carbon atoms and phenyl, $R_7$ is a group selected from hydrogen, halogen including F, Cl and Br, lower alkoxy having from 1 to 3 carbon atoms and —$CF_3$ groups, and X is O or S, and pharmaceutically acceptable acid addition salts thereof.

The dopamine (DA) hypothesis of schizophrenia suggests that schizophrenia is due to malfunctions of one or more of the DA systems of the brain, and that the antipsychotic effect of the neuroleptics results from the antidopaminergic, i.e. DA-receptor blocking, activity, although it has never been proved. In contrast to classical neuroleptics the new compounds of formula I do not inhibit apomorphine or amphetamine induced stereotypies or hypermotility which means that the compounds are not potent antagonists of the striatal neuroleptic DA-receptor sites. These receptor sites are responsible for extrapyramidal side effects. On the other hand the new compounds of formula I have affinity for other subpopulations of receptors, e.g. those of the prefrontal and limbic parts of the brain. Furthermore, the compounds have been found to be potent in interfering with the function of those subpopulations of DA neurons preferentially influenced by ergometrine. The compounds have also an indirect effect on DA transmission by their influence on the glutaminergic transmission, in which a hypofunction has been found in schizophrenic patients.

The new compounds of formula I decrease exploratory behaviour and in somewhat higher doses inhibit conditioned avoidance response. These properties and the suggested influences on particular subpopulations of DA neurons and DA receptors suggest that the compounds have antipsychotic properties.

Endogenous depression seems to be a biochemically heterogeneous disorder. It has been suggested that depressed patients can be divided in two subpopulations: one characterized by a low noradrenaline (NE) turnover and a second characterized by a low serotonin (5HT) turnover in the brain. The effect of antidepressnats on presynaptic alfa$_2$-receptors has been shown to be important in the control of NE release. Tricyclic antidepressants inhibit uptake of NE and thereby increase the concentration of NE in the synaptic cleft (J. J. Shildkraut, Amer. J. Psychiatr. 122, 509 (1965)), which could explain the antidepressant action of these drugs. However, the relationship between clinical effect and ability to inhibit NE uptake is poor (K. Ghose et al., Psychopharmacology 54, 57 (1977)). At least one particular subgroup of depressed patients are deficient in central 5HT function (H. H. Van Praag and J. Korf, Int. Pharmacopsychiatr. 9, 35 (1974)).

The new compounds of formula I facilitate both central NE and 5HT transmission in the central nervous system (CNS). Like other antidepressants, the new compounds of formula I inhibit aggression and muricidal behaviour, two animal tests in which 5HT neurons have been shown to participate (P. C. Marks et al., Brain Res. 149, 270 (1978); J. L. Gibbons et al., Fed. Proc. 38, 257 (1979)). Like the established antidepressant drugs mianserin and amitriptyline the compounds are also potent blockers of central 5HT receptors which has been shown by the head-shaking test with mice.

Stress is a state manifested by a specific syndrome consisting of induced changes in a biologic system resulting in diseases of adaption (L. Mikulaj et al., Adv. Exper. Med. Biol. 33, 631 (1973)). The stress often results in systemic damage including increased membrane permeability, catabolism, changes of body temperature, hyperkalemia, gastro-intestinal erosions etc. Many of these manifestations are due to disturbances in the hippocampus-hypothalamic-hypophyseal-adrenocortical axis and are mediated through increased sympathetic tone, adrenocortical hyperactivity and other changes in hormonal and nervous activity. Most of the concomitanly induced changes occur in the thymus gland and the lymph nodes, in the blood count and in the gastrointestinal tract.

Among domestic animals pigs are exposed to a wide variety of stresses, e.g. after weaning, at transports and at regrouping of animals. By studying social parameters such as aggression, hierarchy, interaction, cleanliness in their living space and feeding behaviour in different stress situations the new compounds of formula I have been compared with established drugs, e.g. azaperone and acepromazine, now used in handling pigs.

The new compounds of formula I showed a significant improvement in the stabilization of the social parameters mentioned above, besides the important fact that aggression was totally blocked without any effect on motoric performance. Azaperone and acepromazine blocked aggression by an unspecific mechanism of sedation but did not improve any social parameter.

The convincing effect of the new compounds of formula I in rat and pig testmodels underline the value of the compounds in treatment of stressed animals as well as of psychosomatic disorders in man.

There is much evidence that there exist some connections between pain and depressions (L. von Knorring, Thesis, Umea, Sweden, 1975). A significant overrepresentation of pain has been shown in patients in psychiatric wards (R. Delaplaine et al., Pain 4, 361 (1978)) and as much as 76% of patients with somatic pains showed symptoms of depression. From literature there is evidence that both 5HT and NE modulate transmission of pain in CNS. Up to now the most convincing clinical results in the treatment of pain have been obtained with drugs facilitating 5HT transmission (R. A. Sternbach et al., In: J. J. Bonica et al., eds. Advances in pain research and therapy, New York, pp. 601 (1976)).

According to the invention the new compounds of formula I have been found to have potent analgetic properties. The analgetic effect is evaluated from the writhing syndrome which can be abolished by analgetics. The analgetic properties of the compounds are not reversed by naloxone. Furthermore, contrary to morphine the compounds have not been found to create physical dependence on chronic administration. On the contrary the compounds are promising in the treatment of drug abuse and of drug abstinens.

The new compounds of formula I are potentially antiarrhythmics as they prolong the effective refractory period in the guinea pig papillary muscle at such a low concentration at $10^{-7}$ M. At the pacing frequencies 1, 2 and 4 Hz the prolongations of the refractory period were 30 ms after administration of the new compound of formula I, table I compound II. The well known antiarrhythmics in this experimental situation (P. Arlock, B. Gullberg and S.-O. R. Olsson, Naunyn-Schmiedeberg's Arch. Pharmacol. 304, 27-36 (1978)) change the effective refractory period in the following ways: amiodarone $10^{-5}$ M+35 ms, quinidine $10^{-6}$ M+14 ms and lidocain $10^{-7}$ M+20 ms. Consequently, as the prolongation of the refractory period is an accepted method to measure antiarrhythmic properties (L. Szekeres, J. Papp, Experimental Cardiac Arrhythmias and Antiarrhythmic Drugs, Akadimiai Kiado, Budapest, 1971) these compounds are interesting antiarrhythmics.

Besides, these new compounds also have a positive inotropic effect.

These effects in combination with the antistress effects, which may decrease the sympathetic tones, are valuable for different stress induced cardiovascular disorders.

A unique binding profile of the new compounds of formula I to specific binding sites of different tissues can be utilized in modulation of ion-dependent processes, secretion, metabolism and aggregation of cells as well as vascularization of different tissues. Some of these effects are manifested in a hypothermic response seen in both mice, rats and pigs, in an increased immunologic competence, in a decrease in allergic reactions, in changes of inflammatory responses and in modulation of anesthesia seen in both mice, rats, pigs and monkeys. The modulating effect produced by the new compounds of formula I on transmitter secretion and function, on the 5HT receptors and on the vasoactive tone indicates that the compounds have alleviating effects on migraine.

According to the present invention the novel compounds of general formula I are prepared according to the following reaction sequences:

Sequence A (a)

By reacting a 1-piperazinecarboxamide of formula II

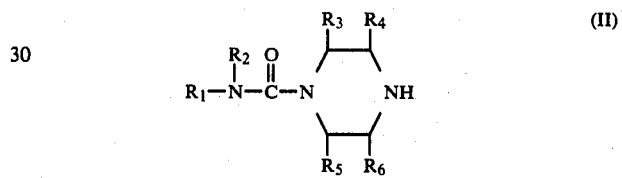

with a 4-substituted 1,1-diarylbutane of formula III

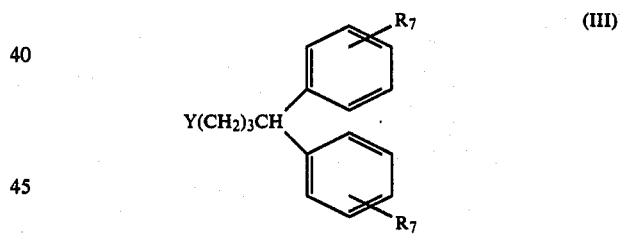

wherein $R_1$, $R_2$, $R_3$, $R_4$, $R_5$, $R_6$ and $R_7$ are as defined above and Y is selected from the group consisting of halogen, e.g. Cl, Br and I, and another reactive grop, e.g. a mesyl or tosyl ester group, to produce a compound of formula I.

Sequence A (b)

By reacting a 1-(4,4-diaryl-butyl)piperazine of formula IV

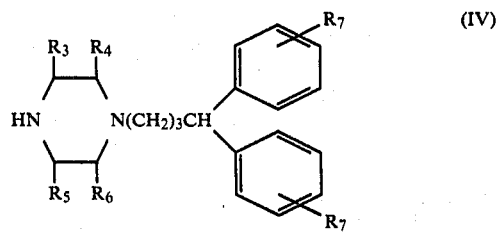

with an isocyanate or isothiocyanate $R_1$-NCX, wherein X is O or S, or with a carbamoyl chloride or thiocarbamoyl chloride

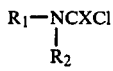

to produce a compound of formula I.

Sequence A (c)

By reacting a 1-(4,4-diaryl-butyl)piperazine of formula IV with an alkali metal cyanate, preferably potassium cyanate, Metal-OCN to produce a compound of formula I wherein $R_1$ and $R_2$ are hydrogen.

Sequence A (d)

By reacting a 1-(4,4-diaryl-butyl)piperazine of formula IV with a phenyl carbamate of formula VIII

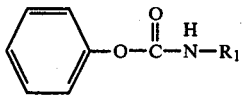 (VIII)

to produce a compound of formula I.

The 1-piperazinecarboxamides of formula II which are used in the method of the invention can be prepared by a sequence of reactions according to any of the following:

Sequence B (a)

A reaction between an isocyanate $R_1$-NCO and a 1-benzylpiperazine of formula V

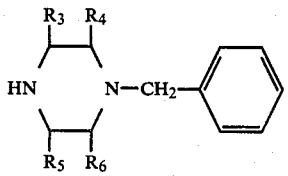 (V)

in ether or the like gives a compound of formula VI

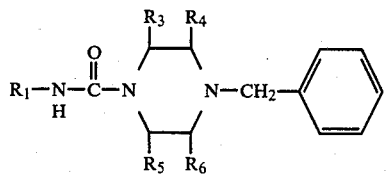 (VI)

Alkylation of the anion generated from the carboxamide of formula VI by treatment first with a suitable strong base, e.g. lithium diisopropylamide, in tetrahydrofuran and then with an alkyl halide $R_2$-Z wherein Z is selected from the group consisting of Br and I leads to the N′,N′-dialkylated compounds of formula VII

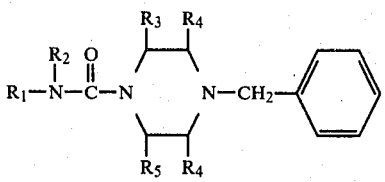 (VII)

The compounds of formulas VI and VII are hydrogenated over a noble metal catalyst to give the compound of formula II.

SEQUENCE B (b)

A reaction between a carbamoyl chloride

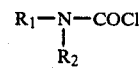

and a 1-benzylpiperazine of formula V in chloroform or the like gives a compound of formula VII. Debenzylation over a nobel metal catalyst gives the compound of formula II.

In sequence A (a) the compound of formula II is reacted with a compound of formula III (synthesised according to French Patent M No. 3695) in a suitable solvent, e.g. a lower alkanol, such as methanol, ethanol, n-butanol and the like, in the presence of an acid acceptor, i.e. an appropriate base, e.g. an alkali metal carbonate or bicarbonate, which may be utilised to bind the acid that is liberated during the course of the reaction to give the compound of formula I. Elevated temperatures may be employed to enhance the rate of reaction.

In sequence A (b) the compound of formula IV (synthesised acording to Neth. Appln. 6,507,312) is reacted with an isocyanate (or an isothiocyanate) $R_1$-NCX or a carbamoyl chloride (or a thiocarbamoyl chloride)

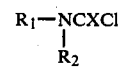

in a suitable solvent, e.g. diethyl ether, chloroform, toluene and the like to give the compounds of formula I. The mixture is reacted over a wide range of temperatures from about 10° C. to about 110° C., although it is possible to employ temperatures above and below this range.

In sequence A (c) the compound of formula IV is reacted with an alkali metal cyanate in an aqueous medium containing acetic acid to form the compound of formula I.

In sequence A (d) the compound of formula IV is reacted with a phenyl carbamate of formula VIII in a suitable solvent e.g. an aromatic hydrocarbon, i.e. benzene, toluene, xylene and the like in the presence of an appropriate base e.g. an alkali metal carbonate to form the compound of formula I. Elevated temperatures are employed to enhance the rate of reaction.

Male mice subjected to prolonged isolation develop aggressive behavior against each other when paired. All clinically used antidepressants an neuroleptics studied in this test inhibit this aggressive behaviour although their activity may differ. Also anxiolytic drugs, e.g. diazepam, are active on this kind of aggressive behaviour. The clinical correlation of this test indicates tranquillizing and anxiolytic activities as well as antiaggressive properties as such (R. L. Duncan et al., J. Med. Chem. 13, 1 (1970)).

This type of aggression is interesting because it is known that this kind of emotional behaviour might be located in limbic structures in the brain (P. D. Mac Lean, Psychosom. Med. 11, 338 (1949)).

Every week 24 male NMR mice, weighting 20–22 g, were isolated in Makrolon cages for three weeks with diet and water ad libitum. A piece of cardboard was placed between the cages to prevent visual contact.

To test aggressiveness the mice were paired in a neutral area, a beaker (14 cm high and diameter 14 cm). A pair is considered aggressive if both the animals show clear signs of fighting within 5 min. This fighting is characterized by biting and vocalization. As soon as fighting is seen, the mice are separated and brought to their home cage. (Every second mouse is marked.) If only one of two mice exhibit aggressive behaviour the aggressive one is paired with another to make a well matched, aggressive pair. Animals showing no aggression are discarded. The frequency of paired mice exhibiting fighting varies from 50–100 percent depending on the time of the year. The test substance is administered s.c. (0.2–0.4 ml/20 g). The mice are paired ½ h, 1 h, 2 h, 4 h, 6 h and 24 h after the injection for trials of 5 min. duration.

The $ED_{50}$-value (mg/kg) reported is the dose inhibiting aggressive behaviour among 50 percent of the pairs 1.0 hour after drug administration.

For the purpose of detecting new psychotropic substances with antiaggressive properties, pharmacologist have used several different models. One model used, the mouse-killing (muricide) by rats, is based on an existing interspecies aggression (P. Karli, Behaviour 10, 81 (1956)). This form of aggressive behaviour which is considered to be of predatory nature, is physiologically and topographically different from other forms of aggression (M. O'Boyle, Psychol. Bull. 81, 261 (1974)). Mousekilling is a spontaneous behaviour in some rat strains e.g. male hooded Long-Evans rats.

Male hooded Long-Evans rats placed in individual cages were used. By testing a number of rats, a colony of rats was obtained that killed a mouse whenever introduced into the rats' cage, by biting the mouse through the cervical spinal cord.

Each rat was tested for mouse-killing behaviour (killing a mouse within 5 minutes) prior to each experiment, thus serving as its own positive control. For each dose level 6 positive rats were selected and the test substance was administered by subcutaneous injection. Doses were selected to form a dose-response curve and the mean effective dose ($ED_{50}$, mg/kg) was calculated by means of linear regression. The rats were tested at 1, and 2 hours after being injected subcutaneously.

When mice are placed in a new area, they explore the whole available territory. Minor and major tranquillizers inhibit the exploratory activity. The sedative effect of drugs is evaluated by the inability of mice to ascend a netladder. The process of climbing is very complex and consists of psychical and taxic (motor performance) components. For the experiments a transparent cage (36×27×23 cm) and a net-ladder (35×6 cm) standing with an inclination of 45° was used. (P. Kneip. Arch. Int. Pharmacodyn. 76, 238 (1960); F. Sandberg, Arzneimittelforsch. 4, 203 (1959)).

The test compound is administered s.c. (10 ml/kg) to 6 NMRI female mice per dose. The mice are marked with a number code from 1 to 6, in order to recognize each individual mouse. In 25 minutes, 55 minutes, 1 h 55 minutes and 3 h 55 minutes time after the administration the mice are placed in the above-mentioned cage for 10 minutes. The number of mice ascending the top of the net-ladder is noted. Other behavioural items are also noted. The $ED_{50}$ (mg/kg) reported is the dose rendering 50% of the mice incapable of entering the top of the net-ladder 0.5 h after the administration.

The Geller conflict test for anxiolytics clearly meets the requirements for a standard model and is most useful operant paradigm in screening for new drugs. (I. Geller and J. Seifler, Psychopharmacologia 1, 482 (1960); B. Blackwell and W. E. Whitehead, In: A. Sudilovsky, S. Gershorn and B. Beer, eds. Predictability in Psychopharmacology: Preclinical and Clinical Correlations. Raven Press New York pp. 121, (1975)).

If an animal is in a stage of exhaustion the rise in glucocorticoids induced by the stress causes thymolymphatic involution and elicites a characteristic change in blood count. These parameters have been used to evaluate the properties of some compounds in their ability to protect against induced stress. In the experiments NMRI female mice were used with well-documented thymic glands. In the experiments the mice were divided in four groups. In the first group the mice were allowed to stay in their home cages all the time. In the second group saline-treated mice were repeatedly forced to swim in water at a temperature of +5° C. for 1 min. once every hour, 6 times per day for four days. In the third group the mice were pre-treated once with the test compound 10 min. before the first swim-test, otherwise the mice were manipulated in the same way as in the second group. In the fourth group the mice were adrenalectomized three days before the start of the swim tests. Otherwise also this group was manipulated as the second group. All mice were killed on the 5th day of the experiment and the weight of the thymic gland registered. The relative weights of the thymic gland in the different groups are recorded in table V. From the table it is evident that repeated swimming in ice-cold water is very stressful and affects the thymic gland dramatically in mice as the relative weight was reduced to about half of that seen in the saline-treated mice not participating in the swim-test. The results (Table V) also confirm that in the absence of adrenals, stress no longer causes thymolymphatic involution. The most protecting capacity against the induced stress was shown by the new compound of formula I (Table V compound II). In this case the protecting potency showed to be significant. Other compounds like diazepam, azaperone and propranolol nowadays used as antianxiety drugs and as drugs against stress showed in these experiments less effective to protect against the induced stress.

A number of methods have been described for studies of somatic expression of adverse stimulation in experimental animals. One method is based upon the development of gastric lesions in rat subjected to some form of environmental stress. The most frequently used mode of stressing the rats is by simple physical restraint. In the experiments to be described rats were immobilized in rigid plastic devices. As repeatedly shown the restraint and the exposure to cold, act synergistically to produce gastric ulcers. The method for production of stress ulcus in rats has been described earlier (R. J. Levine In: C. J. Pfeiffer ed., Peptic Ulcer, Scand. Univ. Books, Copenhagen 1971). The animals in the experiments, female Sprague Dawley rats 180–230 g, have been kept immobilized for three hours at +5° C. For 24 hours prior to restraint the animals furthermore were not allowed to ingest anything but tap water. In all experiments the rats were divided in three groups. In the first group all animals were pre-treated only with saline 15 min. before the exposure to the stressors. In the second group all animals were pre-treated with the referens compound morphine, which after a single administration has very promising properties but in practice connot be used owing to development of tolerance and addiction. The third group consisted always of the compound to be tested in this model. The number and severity of gastric erosions in the opened stomach of controls and drug-pre-treated animals were scored. The average number of gastric ulcers in the control rats were put equal to a hundred percent. In table VI the potency of some compounds to protect against gastric ulcers in the described experiments is reported. All pre-treatments were always made 15 min. before the exposure to cold and restraint.

The writhing test is a frequently used test of analgetic properties (L. B. Witkin et al., J. Pharmacol. Exp. Ther. 133, 400 (1961)). If acetic acid (0.5%, 15 ml/kg) is injected intraperitoneally in mice (NMRI) they will without exception develop a writhing behaviour characterized by stretching their hind legs. The drugs to be tested were administered subcutaneously to 6 female mice at each dose 20 min. before the injection of the acetic acid. After 10 min. The behaviour of the mice was studied in 5 min. The $ED_{50}$ value is the dose blocking the writhing behaviour in 50% of the animals during the 5 min. study period.

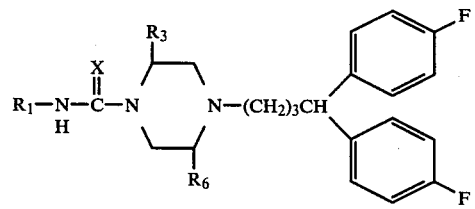

TABLE I.

| Isolation-induced aggressive behaviour | | | | | |
|---|---|---|---|---|---|
| Compound | $R_1$ | $R_3$ | $R_6$ | X | $ED_{50}$, mg/kg, sc |
| I | $CH_3$ | H | H | O | 4.8 |
| II | $C_2H_5$ | H | H | O | 1.3 |
| III | $CH_3$ | $CH_3$ | $CH_3$ | O | 2.6 |
| IV | $CH_3$ | H | H | S | 2.0 |
| Amitriptyline | | | | | 5 |
| Imipramine | | | | | 15 |
| Chlorpromazine | | | | | 1,4 |

TABLE II.

| Spontaneous mouse-killing | | | | | | |
|---|---|---|---|---|---|---|
| | | | | | $ED_{50}$, mg/kg, s.c. | |
| Compound | $R_1$ | $R_3$ | $R_6$ | X | 1 hr | 2 hrs |
| I | $CH_3$ | H | H | O | 0.5 | 0.7 |
| II | $C_2H_5$ | H | H | O | 0.4 | 1.9 |
| III | $CH_3$ | $CH_3$ | $CH_3$ | O | 1.9 | 2.9 |
| IV | $CH_3$ | H | H | S | 0.1 | 0.1 |
| Amitriptyline | | | | | >10 | 6.4 |

TABLE III.

| Climbimg | | | | | |
|---|---|---|---|---|---|
| Compound | $R_1$ | $R_3$ | $R_6$ | X | $ED_{50}$, mg/kg, s.c. |
| I | $CH_3$ | H | H | O | 1.5 |
| II | $C_2H_5$ | H | H | O | 0.7 |
| III | $CH_3$ | $CH_3$ | $CH_3$ | O | 1.0 |
| IV | $CH_3$ | H | H | S | 5.1 |
| Haloperidol | | | | | 1.3 |
| Chlorpromazine | | | | | 2.0 |

TABLE IV.

| Geller conflict test | | | | | |
|---|---|---|---|---|---|
| Compound | $R_1$ | $R_3$ | $R_6$ | X | Dose mg/kg, s.c. | Percent shocks compared to controls |
| II | $C_2H_5$ | H | H | O | 0.5 | 250** |
| Diazopam | | | | | 1.0 | 240** |

The significance was tested by student's t-test.

TABLE V.

| Swim-test | | | | | | |
|---|---|---|---|---|---|---|
| Compound | $R_1$ | $R_3$ | $R_6$ | X | Pre-treatment dose, mg/kg | Relative weight of thymus, × 100 |
| Saline[a] | | | | | | 66 |
| Saline | | | | | | 36 |
| Saline[b] | | | | | | 64 |
| II | $C_2H_5$ | H | H | O | 1.0 | 50** |
| Azaperone | | | | | 1.0 | 48* |
| Diazepam | | | | | 1.0 | 45* |
| Propranolol | | | | | 10.0 | 48* |

[a]untreated not participating in the swim test.
[b]adrenalectomized animals
The significance was tested by Wilcoxon's ranking test.

TABLE VI.

| Stress-induced ulcers | | | | | | |
|---|---|---|---|---|---|---|
| Compound | $R_1$ | $R_3$ | $R_6$ | X | Pre-treatment dose mg/kg | Inhibition, % |
| II | $C_2H_5$ | H | H | O | 1.0 | 43 |
| Azaperone | | | | | 1.0 | 0 |
| Morphine | | | | | 2.0 | 67 |

TABLE VII.

| Analgetic properties | | | | | |
|---|---|---|---|---|---|
| Compound | $R_1$ | $R_3$ | $R_6$ | X | $ED_{50}$, mg/kg, s.c. |
| I | $CH_3$ | H | H | O | 0.5 |
| II | $C_2H_5$ | H | H | O | 0.7 |
| III | $CH_3$ | $CH_3$ | $CH_3$ | O | 1.0 |
| IV | $CH_3$ | H | H | S | 1.4 |
| Morphine | | | | | 1.6 |

The formula I bases are convertible to therapeutically active non-toxic acid addition salts by treatment with an appropriate acid, e.g. an inorganic acid, such as a hydrohalic acid, especially hydrochloric and hydrobromid acid, or sulfuric acid, nitric acid, phosphoric acid and the like, or an organic acid, such as acetic, propionic, glycolic, lactic, malonic, succinic, fumaric, tartaric, citric and the like acids. Conversely, the salt form can be converted by treatment with alkali into the free base form.

Effective quantities of any of the foregoing pharmacologically active compounds of formula I may be administered to a human being or animal for therapeutic purposes according to usual routes of administration and in usual forms, such as orally in solutions, emulsions, suspensions, pills, tablets and capsules, in pharmaceutically acceptable carriers and parenterally in the form of sterile solutions. For the parenteral administration of the active substance the carrier or excipient may be a sterile, parenterally acceptable liquid, e.g. water, or a parenterally acceptable oil, e.g. arachidic oil.

Although very small quantities of the active materials of the present invention are effective when minor therapy is involved or in the cases of administration to subjects having a relatively low body weight, unit dosages are usually from 2 milligrams upwards preferably 25, 50 or 100 milligrams or even higher depending on the condition to be treated and the age and weight of the patient as well as the response to the medication.

The unit dose may be from 0.1 to 200 milligrams, preferably from 10 to 50 milligrams. Daily dosages should preferably range from 10 milligrams to 200 milligrams. The exact individual dosages as well as daily dosages will, of course, be determined according to standard medical principles under the direction of a physician of veterinarian.

The following formulations are representative for all of the pharmacologically active compounds of this invention. Example of a suitable capsule formulation:

|  | per capsule, mg |
| --- | --- |
| Active ingredient, as salt | 10 |
| Lactose | 250 |
| Starch | 120 |
| Magnesium stearate | 5 |
| Total | 385 |

In case of higher amounts of active ingredient, the amount of lactose used may be reduced.

Example of a suitable tablet formulation:

|  | per tablet, mg |
| --- | --- |
| Active ingredient, as salt | 10 |
| Avicel | 108 |
| Colloidal silica | 10 |
| Talc | 20 |
| Magnesium stearate | 2 |
| Total | 150 |

Example of a suitable injection formulation:

|  | per 100 ml |
| --- | --- |
| Active ingredient, as salt | 1000 mg |
| Metagin | 100 mg |
| NaCl | 700 mg |
| HCl 1/10 N to pH 3.5 |  |
| Aq. sterilisata ad | 100 ml |

The pharmaceutical preparations may also contain therapeutically useful substances other than the pharmacologically active compounds of formula I.

BRIEF DESCRIPTION OF THE DRAWINGS

FIGS. 1–4 are the infrared spectra of the compounds of Examples 5, 6, 8 and 10, respectively.

Figure 3:
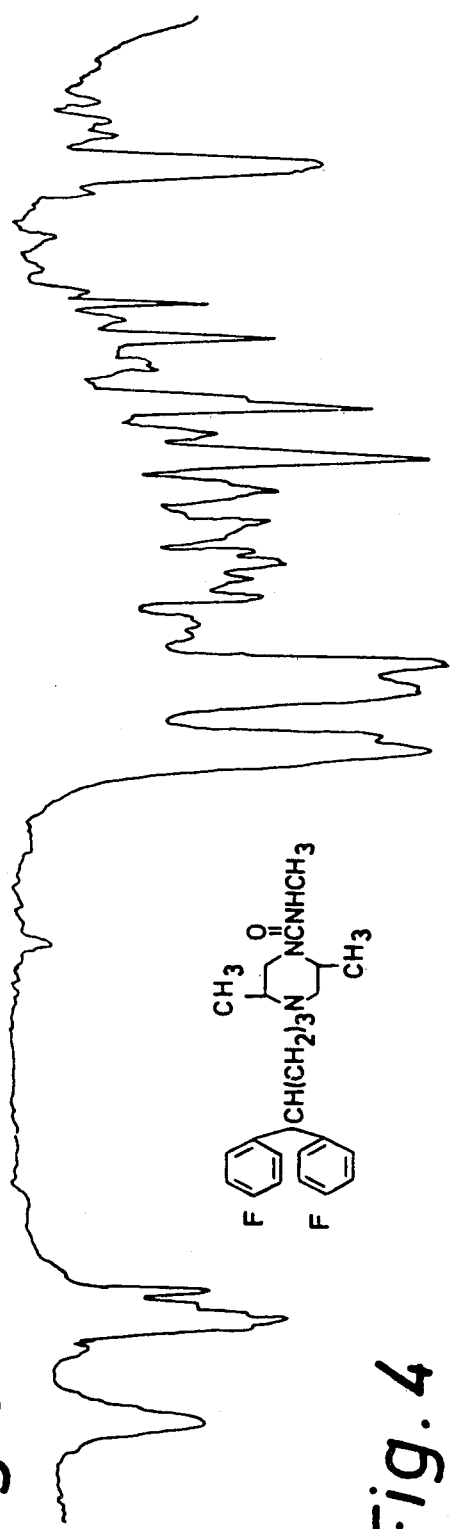

The following examples are intended to illustrate the present invention, without limiting the scope thereof.

EXAMPLE 1

N'-Ethyl-4-benzyl-1-piperazinecarboxamide

To a solution of 13.5 g of (0.19 mole) of ethyl isocyanate in 300 ml of ether was added dropwise at 25° C. over a period of 30 minutes 37.0 g (0.21 mole) of 1-benzyl-piperazine. The mixture was refluxed for 2 hours. 250 ml of petroleum ether was added and the mixture was cooled to 5° C. The solid, which precipitated from the solution, was collected by filtration and recrystallised from toluene-petroleum ether 1:1 to give 43 g of N'-ethyl-4-benzyl-1-piperazinecarboxamide. Melting point 100°–102° C.

EXAMPLE 2

N'-Ethyl-N'-methyl-4-benzyl-1-piperazinecarboxamide hydrochloride

To 0.068 mole of lithium diisopropylamide, prepared from n-butyllithium and diisopropylamine in tetrahydrofuran, was added at −40° C. 14.9 g (0.060 mole) of N'-ethyl-4-benzyl-1-piperazinecarboxamide in 100 ml of tetrahydrofuran over a period of 30 minutes. The mixture was warmed to 0° C. during 30 minutes. After cooling to −30° C. 11.6 g (0.082 mole) of methyl iodide was added during 20 minutes. The mixture was allowed to stand at room temperature over night. The mixture was poured onto ice and extracted with ether. The combined extracts were dried over sodium sulphate and the ether removed by distillation. The residual oil was dissolved in ether and the hydrochloride was precipitated with ethanolic HCl. The solid was collected by filtration and recrystallized from isopropanol to give 14.0 g of N'-ethyl-N'-methyl-4-benzyl-1-piperazinecarboxamide hydrochloride.

EXAMPLE 3

N',N'-Diethyl-4-benzyl-1-piperazinecarboxamide

A solution of 26.4 g (0.15 mole) of 1-benzylpiperazine in 70 ml of chloroform was heated until it began refluxing and a solution of 20.4 g (0.15 mole) of diethylcarbamoyl chloride in 80 ml of chloroform was added. The mixture was refluxed for 2 hours. The cooled mixture was made basic with sodium hydroxide (0.25 mole, 10.0 g in 60 ml of water) and extracted with chloroform. The chloroform extracts were dried over sodium sulphate, the solvent removed and the residue distilled to give 25.4 g of N',N'-diethyl-4-benzyl-1-piperazinecarboxamide, b.p. 140°–150° C. at 0.12 mm Hg.

EXAMPLE 4

N'-Ethyl-1-piperazinecarboxamide 22.3 g (0.09 mole) of N'-ethyl-4-benzyl-1-piperazinecarboxamide dissolved in 370 ml of ethanol and acidified with ethanolic HCl was treated with hydrogen over a palladium catalyst in a Parr hydrogenator at 35–40 psi. The catalyst was removed by filtration and the solvent removed under reduced pressure. The residue was dissolved in 25 ml of water and was made basic with 10 g (0.25 mole) of sodium hydroxide in 50 ml of water. The mixture was extracted with chloroform. The combined extracts were dried over sodium sulphate and concentrated. The white product was recrystallised from isobutylacetate to give 10.0 g of N'-ethyl-1-piperazinecarboxamide. Melting point 81°–83° C.

EXAMPLE 5

N'-Ethyl-4-[4,4-(di-p-fluorobenzyl)butyl]-1-piperazinecarboxamide hydrochloride

A stirred mixture of 4.7 g (0.03 mole) of N'-ethyl-1-piperazinecarboxamide, 10.1 g (0.036 mole) of 4-chloro-1,1-(di-p-fluorophenyl)butane, 5.0 g of sodium bicarbonate and 10 ml of ethanol was heated at reflux for 60 hours, 50 ml of water was added. The mixture was extracted twice with ether. The combined extracts were dried over sodium sulphate and concentrated. The residue was dissolved in ethanol-ether and the hydrochloride was precipitated with ethanolic HCl. The solid was collected by filtration and recrystallised from 2-butanone-isopropanol 4:1 to give 6.4 g of N'-ethyl-4-[4,4-(di-p-fluorophenyl)butyl]-1-piperazinecarboxamide hydrochloride. Melting point 177°–178° C. Infrared spectrum FIG. 1.

EXAMPLE 6

N'-Methyl-4-[4,4-(di-p-fluorophenyl)butyl]-1-piperazinecarboxamide

To a solution of 20.0 g (0.06 mole) of 1-[4,4-(di-p-fluorophenyl)butyl]-piperazine in 150 ml of ether was added dropwise over a period of 30 minutes 4.5 g (0.079 mole) of methyl isocyanate in 10 ml of ether. The mixture was allowed to stand at room temperature. On short standing a white crystalline precipitate appeared which was collected by filtration and recrystallized from ethanol-ether to give 21.0 g of N'-methyl-4-[4,4-(di-p-fluorophenyl)butyl]-1-piperazinecarboxamide. Melting point 160°–162° C. Infrared spectrum FIG. 2.

EXAMPLE 7

N'-Phenyl-4-[4,4-di-p-fluorophenyl)butyl]-1-piperazinecarboxamide hydrochloride

To a solution of 5.0 g (0.015 mole) of 1-[4,4-(di-p-fluorophenyl)butyl]-piperazine in 30 ml of ether was added dropwise 2.0 g (0.017 mole) of phenyl isocyanate in 2 ml of ether. The mixture was refluxed for 1 hour. After standing over night the mixture was acidified with ethanolic HCl. The solid, which precipitated, was collected by filtration and recrystallised from ethanol to give 5.6 g of N'-phenyl-4-[4,4-(di-p-fluorophenyl)-butyl]-1-piperazinecarboxamide hydrochloride. Melting point 202°–204° C.

EXAMPLE 8

Trans-2,5-Dimethyl-N'-methyl-4-[4,4-(di-p-fluorophenyl)butyl]-1-piperazinecarboxamide oxalate To a solution of 5.0 g (0.014 mole) of trans-2,5-dimethyl-1-[4,4-(di-p-fluorophenyl)butyl]-piperazine in 25 ml of ether was added dropwise a solution of 0.9 g (0.010 mole) of methyl isocyanate in 5 ml of ether. After stirring for 30 minutes, the mixture was refluxed for 2 hours. The ether was removed under reduced pressure. An analytical sample of the oily residue was isolated by preparative thin layer chromatography (tlc). Preparative tlc was performed on plates covered with a 2.0 mm thick layer of silica gel (Merck $F_{254}$). Eluent, chloroformdiethylamine-methanol (17:2:1). The zone of silica gel containing the product was detected by UV light, scratched of and eluted with ether. $R_f$-value: 0.67. Infrared spectrum FIG. 3.

The oily residue was dissolved in 10 ml of 2-butanone and 2.5 g (0.028 mole) of oxalic acid in 30 ml of 2-butanone was added. The solid which precipitated was collected by filtration and recrystallised from isopropanol to give 4.0 g of a crystalline complex between trans-2,5-dimethyl-N'-methyl-4-[4,4-(di-p-fluorophenyl)butyl]-1-piperazinecarboxamide and oxalic acid containing about 1.5 mole oxalic acid per mole free base and a certain amount of isopropanol which could only be removed by extreme means. Melting point 153°–155° C.

EXAMPLE 9

4-[4,4-(di-p-fluorophenyl)butyl]-1-piperazinecarboxamide-hydrochloride

To a solution of 5.0 g (0.015 mole) of 1-[4,4-(di-p-fluorophenyl)butyl]-piperazine in 25 ml glacial acetic acid was added dropwise 1.6 g (0.02 mole) of potassium cyanate in 10 ml of water. The mixture was allowed to stand over night at room temperature. The cooled mixture was diluted with 75 ml of water and made basic with 5 N sodium hydroxide. The solid, which precipitated, was collected by filtration, washed with water, and dried. The resulting solid was dissolved in ethanol and the solution was treated with a slight excess of ethanolic HCl. The product, which precipitated, was collected by filtration and recrystallized from ethanol-ether to give 4.7 g of 4-[4,4-(di-p-fluorophenyl)butyl]-1-piperazinecarboxamide hydrochloride. Melting point 195°–197° C.

EXAMPLE 10

Figure 4:
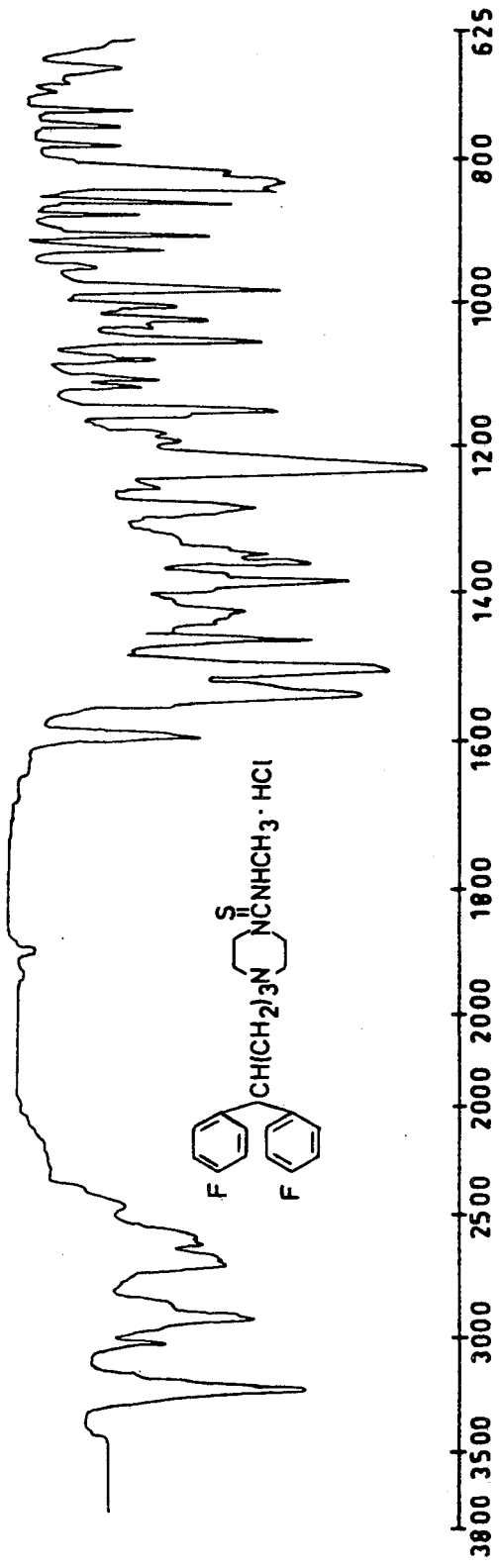

N'-Methyl-4-[4,4-(di-p-fluorophenyl)butyl]-1-piperazinecarbothioamide hydrochloride To a solution of 3.3 g (0.01 mole) of 1-[4,4-(di-p-fluorophenyl)butyl]-piperazine in 25 ml of ether was added dropwise a solution of 0.75 g (0.01 mole) methyl isothiocyanate in 5 ml of ether. The mixture was allowed to stand with stirring over night. The ether was removed under reduced pressure. The oily residue was dissolved in ethanol, and converted to the salt by addition of ethanolic HCl. Ether was added, and the solid, which precipitated, collected by filtration. The salt was recrystallized from methanol to give 3.5 g of N'-methyl-4-[4,4-(di-p-fluorophenyl)butyl]-1-piperazinecarbothioamide hydrochloride. Melting point 214°–216° C. Infrared spectrum FIG. 4.

TABLE II

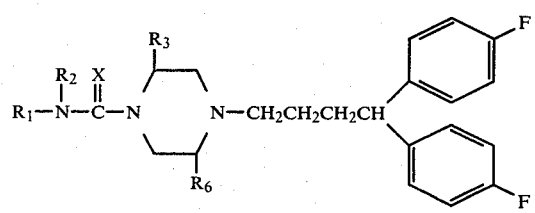

| Example | Method in accordance with example | R₁ | R₂ | R₃ | R₆ | X | M.p.[c] °C. | Salt |
|---|---|---|---|---|---|---|---|---|
| 11 | 6 + 2 | $CH_3$ | $CH_3$ | H | H | O | 129–31 | HCl |
| 12 | 1 + 2 + 4 + 5 | $CH_3$ | $C_2H_5$ | H | H | O | 152–53 | HCl |
| 13 | 3 + 4 + 5 | $C_2H_5$ | $C_2H_5$ | H | H | O | 203–05 | oxalate |
| 14 | 7 | $C_2H_5$ | H | $CH_3$[b] | $CH_3$[b] | O | 184–86 | HCl |
| 15 | 10 | $C_2H_5$ | H | H | H | S | 197–99 | HCl |
| 16 | 7 | $n\text{-}C_3H_7$ | H | H | H | O | 190–92 | HCl |
| 17 | 10 | $n\text{-}C_3H_7$ | H | H | H | S | 185–87 | HCl |
| 18 | 1 + 4 + 5 | $iso\text{-}C_3H_7$ | H | H | H | O | 206–08 | HCl |
| 19 | 7 | $iso\text{-}C_3H_7$ | H | $CH_3$[b] | $CH_3$[b] | O | 184–86 | HCl |
| 20 | 10 | $iso\text{-}C_3H_7$ | H | H | H | S | 202–04 | HCl |
| 21 | 7 | $cyclo\text{-}C_3H_5$ | H | H | H | O | 192–94 | HCl |
| 22 | 7 | $cyclo\text{-}C_3H_5$ | H | $CH_3$[b] | $CH_3$[b] | O | 172–75 | HCl |
| 23 | 10 | $cyclo\text{-}C_3H_5$ | H | H | H | S | 187–89 | HCl |
| 24 | 7 | $n\text{-}C_4H_9$ | H | H | H | O | 185–87 | HCl |
| 25 | 10 | $n\text{-}C_4H_9$ | H | H | H | S | 156–58 | HCl |
| 26 | 7 | $tert\text{-}C_4H_9$ | H | H | H | O | 191–93 | HCl |
| 27 | 7 | $CH_2\text{—}cyclo\text{-}C_3H_5$ | H | H | H | O | 196–98 | HCl |
| 28 | 7 | $n\text{-}C_5H_{11}$ | H | H | H | O | 172–74 | HCl |
| 29 | 7 | $cyclo\text{-}C_6H_{11}$ | H | H | H | O | 172–73 | HCl[c] |
| 30 | 7 | $n\text{-}C_8H_{17}$ | H | H | H | O | 187–89 | HCl |
| 31 | 7 | $CH_2\text{=}CHCH_2$ | H | H | H | O | 187–89 | HCl |
| 32 | 10 | $C_6H_5$ | H | H | H | S | 206–08 | HCl |
| 33 | 7 | $p\text{-}Cl\text{—}C_6H_4$ | H | H | H | O | 116–18 | HCl |
| 34 | 7 | $CH_2\text{—}C_6H_5$ | H | H | H | O | 185–87 | HCl |
| 35 | 7 | $CH_2CH_2\text{—}C_6H_5$ | H | H | H | O | 139–41 | HCl |

[a]Melting points are uncorrected
[b]trans-2,5-dimethyl
[c]Hydrate (about one $H_2O$)

EXAMPLE 36

N'-ethyl-4-[4,4-(di-p-fluorophenyl)butyl]-1-piperazinecarboxamide hydrochloride

A stirred mixture of 9.9 g (0.03 mole) of 1-[4,4-(di-p-fluorophenyl)butyl]piperazine, 5.0 g (0.03 mole) of phenyl N-ethylcarbamate, 6.6 g of potassium carbonate and 100 ml of toluene was heated at reflux for 45 minutes. The mixture was filtered and the solvent was removed. The residual oil was dissolved in ethanol-water and the hydrochloride was precipitated with ethanolic HCl. The solid was collected by filtration and recrystallized from 2-butanone-isopropanol 4:1 to give 6.8 g of N'-ethyl-4-[4,4-(di-p-fluorophenyl)butyl]-1-piperazinecarboxamide hydrochloride. Melting point 177°–178° C.

What we claim is:

1. A pharmaceutical composition for treatment of pain and for treatment of arrhythmia which comprises a pharmaceutically effective amount of a compound of formula I

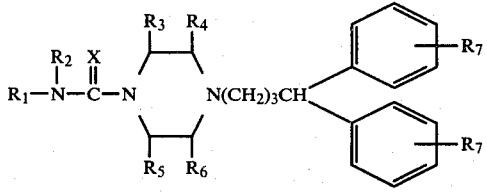

wherein $R_1$ and $R_2$ are groups independently selected from the group of hydrogen, alkyl straight or branched chains having from 1 to 10 carbon atoms, cycloalkyl having from 3 to 8 carbon atoms, aralkyl having from 7 to 9 carbon atoms, alkenyl having from 2 to 10 carbon atoms, phenyl unsubstituted or substituted by one to three substituents selected from halogen, including F, Cl and Br, lower alkyl having from 1 to 5 carbon atoms, lower alkoxy having from 1 to 5 carbon atoms, amine unsubstituted or substituted by one or two lower alkyl groups having from 1 to 5 carbon atoms, $-CF_3$ and $-CN$ groups, $R_3$, $R_4$, $R_5$ and $R_6$ are groups independently selected from hydrogen, lower alkyl having from 1 to 3 carbon atoms and phenyl, $R_7$ is a group selected from hydrogen, halogen including F, Cl and Br, lower alkoxy having from 1 to 3 carbon atoms and $-CF_3$ groups, and X is O or S, or pharmaceutically acceptable acid addition salts thereof, and a pharmaceutically acceptable carrier.

2. A method of treating human beings and animals for pain by administering an analgesic effective amount of a compound of formula I as defined in claim 1 to said human beings and animals.

3. A method of treating human beings and animals for arrhythmia by administering an anti-arrhythmic effective amount of a compound of formula I as defined in claim 1 to said human beings and animals.

* * * * *